(12) United States Patent
Goldenberg et al.

(10) Patent No.: US 12,029,627 B2
(45) Date of Patent: Jul. 9, 2024

(54) INTRANASAL ADMINISTRATION DEVICE

(71) Applicant: pHi-Tech Animal Health Technologies Ltd., Airport City (IL)

(72) Inventors: Gershon Goldenberg, Pardes Hanna-Karkur (IL); Asaf Halamish, Pardes Hanna-Karkur (IL); Yehuda Ehud Ashash, Sede Nahum (IL); Avner Finger, Pardes Hanna-Karkur (IL)

(73) Assignee: pHi-Tech Animal Health Technologies Ltd., Airport City (IL)

( * ) Notice: Subject to any disclaimer, the term of this patent is extended or adjusted under 35 U.S.C. 154(b) by 569 days.

(21) Appl. No.: 16/895,790

(22) Filed: Jun. 8, 2020

(65) Prior Publication Data

US 2020/0297467 A1    Sep. 24, 2020

Related U.S. Application Data

(63) Continuation of application No. PCT/IB2018/059883, filed on Dec. 11, 2018.
(Continued)

(51) Int. Cl.
*A61D 7/00* (2006.01)
*A61D 1/02* (2006.01)
*A61M 15/08* (2006.01)

(52) U.S. Cl.
CPC ............ *A61D 7/00* (2013.01); *A61D 1/025* (2013.01); *A61M 15/08* (2013.01)

(58) Field of Classification Search
CPC .......... A61D 1/025; A61D 7/00; A61M 5/20; A61M 15/08; A61M 11/006; A61M 11/008; A61M 11/06; A61M 11/08
(Continued)

(56) References Cited

U.S. PATENT DOCUMENTS

| 4,276,879 A | 7/1981 | Yiournas |
| 4,673,395 A | 6/1987 | Phillips |

(Continued)

FOREIGN PATENT DOCUMENTS

| AU | 727855 | 3/1999 |
| CA | 2741441 | 2/2003 |

(Continued)

OTHER PUBLICATIONS

Office action for Chinese Application No. 201880029105.6, issued Dec. 28, 2021 (includes translation) (20 pages).

(Continued)

*Primary Examiner* — David J Parsley
*Assistant Examiner* — Danielle A Clerkley
(74) *Attorney, Agent, or Firm* — Klarquist Sparkman, LLP

(57) ABSTRACT

Disclosed devices for intranasal administration of medicament to a patient can comprise a hand-held unit comprising a gripping portion for being held by an operator, a spray head having a spray apparatus and a nozzle, a control unit coupled to the hand-held unit via at least one connecting tube, and one or more containers for holding medicaments. The at least one connecting tube can be flexible enough to enable easy maneuvering of the hand-held unit and rigid enough to prevent widening of the tube due to inner pressure when medicaments pass from the containers to the hand-held unit.

24 Claims, 8 Drawing Sheets

Related U.S. Application Data

(60) Provisional application No. 62/596,967, filed on Dec. 11, 2017.

(58) Field of Classification Search
USPC .................................... 124/200.14; 604/131
See application file for complete search history.

(56) References Cited

U.S. PATENT DOCUMENTS

| | | | |
|---|---|---|---|
| 4,717,383 A | 1/1988 | Phillips et al. | |
| 4,985,015 A | 1/1991 | Obermann | |
| 5,320,162 A | 6/1994 | Seaman | |
| 5,497,944 A * | 3/1996 | Weston | B05B 11/026 |
| | | | 128/200.22 |
| 5,807,336 A | 9/1998 | Russo | |
| 6,858,020 B2 | 2/2005 | Rusnak | |
| 7,056,307 B2 | 6/2006 | Smith et al. | |
| 7,124,964 B2 | 10/2006 | Bui | |
| 8,029,469 B2 | 10/2011 | Ethelfield | |
| 8,529,522 B2 | 9/2013 | Cohen | |
| 8,820,316 B2 * | 9/2014 | Crockford | A61M 11/005 |
| | | | 128/200.14 |
| 9,706,754 B2 | 7/2017 | Prescott et al. | |
| 10,258,445 B2 | 4/2019 | Halamish et al. | |
| 2001/0008961 A1 | 7/2001 | Hecker | |
| 2002/0183616 A1 | 12/2002 | Toews et al. | |
| 2004/0134494 A1 | 7/2004 | Papania et al. | |
| 2005/0043681 A1 | 2/2005 | Rusnak | |
| 2005/0150489 A1 | 7/2005 | Dunfield et al. | |
| 2005/0209569 A1 | 9/2005 | Ishikawa et al. | |
| 2006/0135910 A1 | 6/2006 | Luther et al. | |
| 2008/0114305 A1 | 5/2008 | Gerondale | |
| 2008/0177223 A1 | 8/2008 | Johnston et al. | |
| 2009/0018505 A1 | 1/2009 | Arguedas et al. | |
| 2009/0163860 A1 | 6/2009 | Patrick | |
| 2009/0198215 A1 | 8/2009 | Chong et al. | |
| 2009/0270796 A1 | 10/2009 | Perry et al. | |
| 2010/0130960 A1 | 5/2010 | Spire | |
| 2012/0073515 A1 | 3/2012 | Chung et al. | |
| 2014/0114258 A1 | 4/2014 | Day | |
| 2015/0128873 A1 | 5/2015 | Prescott et al. | |
| 2015/0174321 A1 | 6/2015 | Cohen | |
| 2016/0101240 A1 | 4/2016 | Samson | |
| 2016/0235512 A1 | 8/2016 | Miller et al. | |
| 2016/0263321 A1 | 9/2016 | Eisele et al. | |
| 2016/0296313 A1 | 10/2016 | Fleming et al. | |
| 2016/0324613 A1 | 11/2016 | Halamish et al. | |
| 2017/0197037 A1 | 7/2017 | Edwards | |
| 2019/0183622 A1 | 6/2019 | Halamish et al. | |

FOREIGN PATENT DOCUMENTS

| | | | |
|---|---|---|---|
| CA | 2959162 | 3/2016 | |
| CN | 1791440 A | 6/2006 | |
| CN | 102105183 | 6/2011 | |
| CN | 202136444 U * | 2/2012 | ............. A61D 1/025 |
| CN | 203208448 U | 9/2013 | |
| CN | 103458940 A | 12/2013 | |
| CN | 104812334 A | 7/2015 | |
| CN | 105597185 A | 5/2016 | |
| CN | 105682607 A | 6/2016 | |
| CN | 106421978 A | 2/2017 | |
| CN | 107468372 A | 12/2017 | |
| CN | 106029004 B | 3/2018 | |
| DE | 202014008893 U1 * | 1/2015 | .......... A61M 11/008 |
| EP | 0747083 A2 | 12/1996 | |
| EP | 2285436 | 10/2015 | |
| EP | 3089703 A1 | 11/2016 | |
| GB | 2233234 | 1/1991 | |
| WO | WO 2003082381 A1 | 10/2003 | |
| WO | WO 2004/101060 | 11/2004 | |
| WO | WO 2008/057223 | 5/2008 | |
| WO | WO 2008/079824 | 7/2008 | |
| WO | WO2009062508 A1 | 5/2009 | |
| WO | 2009/134577 | 11/2009 | |
| WO | WO 2010/052579 | 5/2010 | |
| WO | WO 2012/176029 | 12/2012 | |
| WO | WO 2013/064475 | 5/2013 | |
| WO | WO 2014/016807 | 3/2014 | |
| WO | WO 2014/107766 | 7/2014 | |
| WO | WO 2015/101981 | 7/2015 | |
| WO | WO 2017/086807 | 5/2017 | |
| WO | WO 2017/086924 A1 | 5/2017 | |
| WO | WO 2018/092138 A1 | 5/2018 | |
| WO | WO 2018/203203 A1 | 11/2018 | |
| WO | WO2020002321 A1 | 1/2020 | |

OTHER PUBLICATIONS

Office action for U.S. Appl. No. 16/667,405, issued Jan. 6, 2022 (19 pages).
Office action for Indian Application No. 201917048613, issued Feb. 17, 2022 (includes translation) (5 pages).
Examination Report for European Application No. EP 18794760.1, issued by the European Patent Office on Aug. 6, 2021 (8 pages).
Examination Report for Russian Application No. 2019136958, issued by the Russian Patent Office on Aug. 18, 2021 (20 pages).
Office action for Chinese Application No. 201880029105.6, issued Apr. 13, 2022 (with English translation) (25 pages).
Office Action for Russian Application No. 2020121737 issued on Apr. 26, 2022 (with English translation) (17 pgs).
Third Office Action for Chinese Application No. 201880029105.6 issued on May 18, 2022 (with English translation) (24 pgs).
Office action for Indian Application No. 202017024196 issued on Jun. 15, 2022 (w/ English translation) (7 pages).
Office action for Chinese Application No. 201880079657.8, issued on Jul. 13, 2022 with Eng. Translation (24 pages).
European Search Report, EP 14876301.4, dated Aug. 3, 2017 (3 pages).
International Search Report & Written Opinion, PCT/IB2018/052958, mailed Aug. 12, 2018 (14 pages).
International Search Report & Written Opinion, PCT/IB2018/059883, mailed Mar. 25, 2019 (11 pages).
Office action for European Application No. EPC 14876301.4 issued Mar. 10, 2020 (3 pages).
Office Action for Israeli Application No. 246538, issued Dec. 12, 2019 (4 pages, translation incorporated into Office Action).
Office Action for Mexican Application No. MX/a/2016/008647, issued Jul. 19, 2019 (3 pages) (4 pages of translation).
Office Action for Mexican Application No. MX/a/2016/008647, issued Nov. 7, 2019 (4 pages) (5 pages of translation).
Office action for Brazil Application No. BR112016015342, issued May 13, 2020 (3 pages).
International Search Report & Written Opinion, PCT/IB2020/053177, dated Jul. 19, 2020 (20 pages).
Extended European Search Report, issued Sep. 1, 2020, European Patent Application No. EPC 18794760.1, filed Apr. 28, 2018 (10 pages).
Examination Report for European Application No. EP 18888570.1, issued by the European Patent Office on Oct. 25, 2021 (13 pages).
Office action for Chinese Application No. 201880079657.8 (includes translation), issued Oct. 27, 2021 (13 pages).
Office Action for Chinese Application No. 201880029105.6, issued Jun. 2, 2021 (24 pages, with English translation).
Extended European Search Report, issued Dec. 2, 2022 in European Patent Application No. EPC 20784040.6, filed Apr. 3, 2020 (10 pages).
International Search Report and Written Opinion for PCT/IB2021/057450, dated Nov. 5, 2021 (14 pages).
Decision of Rejection for Chinese Application No. 201880079657.8, issued on Jan. 9, 2023 (20 pages, includes English translation).
Office action for Israel Application No. 274909, issued on Jan. 22, 2023 (3 pages).

* cited by examiner

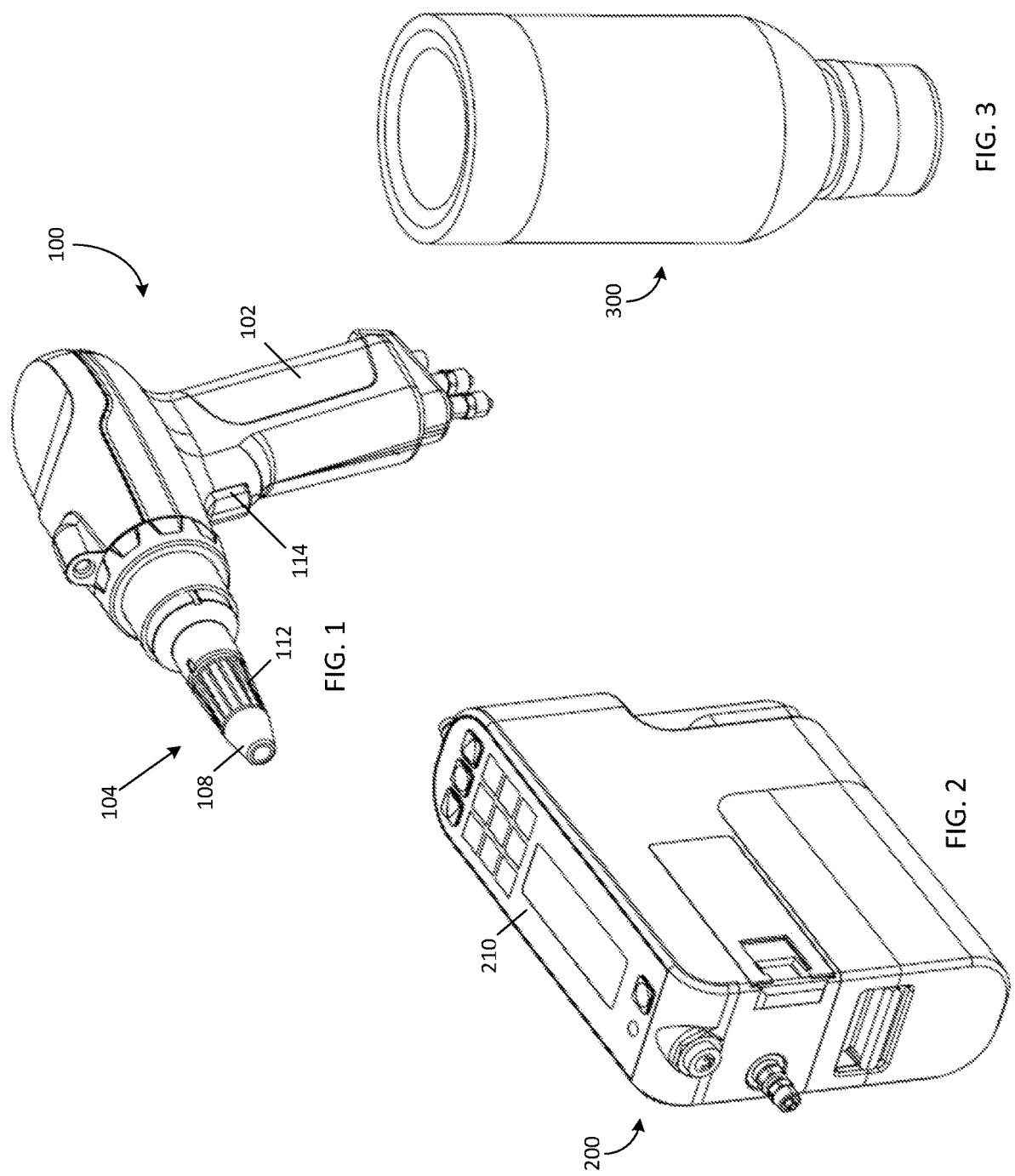

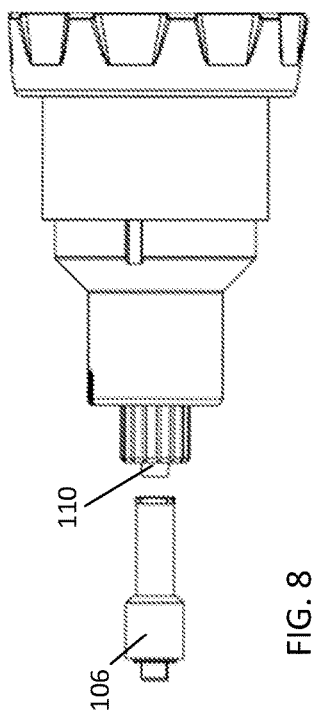
FIG. 8
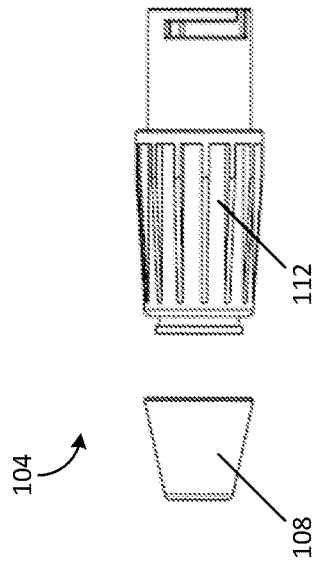
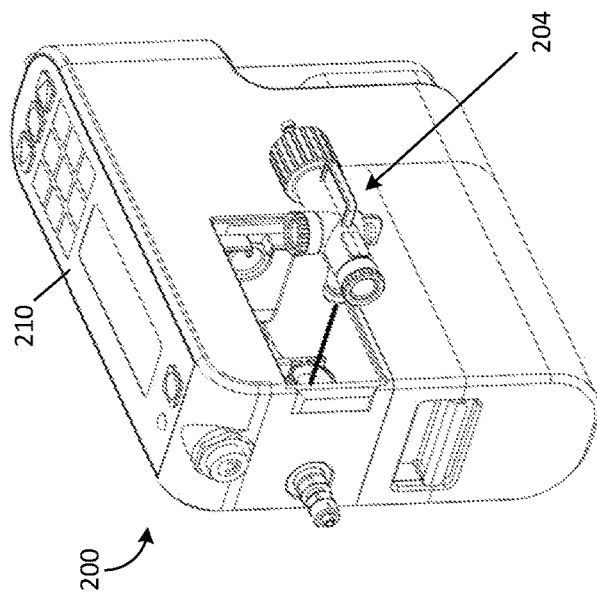
FIG. 10
FIG. 9

INTRANASAL ADMINISTRATION DEVICE

CROSS REFERENCE TO RELATED APPLICATION

The present application is a continuation of International Application No. PCT/IB2018/059883, filed on Dec. 11, 2018, which claims the benefit of U.S. Provisional Application No. 62/596,967, filed on Dec. 11, 2017. Both of these prior applications are incorporated by reference herein in their entireties.

FIELD

The present disclosure concerns vaccination devices for vaccinating patients, particularly livestock animals, and more particularly concerns automated intranasal vaccination devices for vaccinating a large number of feed and companion animals, such as swine, cattle, sheep, goats, equids, poultry, cats, dogs, or aquatic species including fish.

BACKGROUND

In the livestock industry, animals often must be administered substances such as medications, for a variety of reasons. Typically, each producer must treat large numbers of animals. Treatment can often require injecting each animal with a plurality of medications, generally in liquid form. Such medications can include various antigens, drugs, and/or other components, medicines, vaccines, hormones, food supplements and the like (hereinafter referred to generally as "medicament"). Administering such medicaments typically includes using an administration device, such as a syringe or drenching unit, from which a medicament dose is either manually or automatically administered to the animal. This type of administration typically includes hand actuation or pumping of the medication device to deliver the medication to the animal.

When treating a large number of animals (e.g., via a hand-actuated needle device), the operator may become fatigued. This can result in a number of malfunctions, for example: (i) accidental self-injection by the operator; (ii) administering the medicament dose when the needle has not yet penetrated the patient's skin or has not yet penetrated to the desired depth; (iii) administering the dose after the needle has been removed from the patient; (iv) administering only a portion of the required dose; (v) inserting the needle into the patient in a non-optimal orientation; and/or (vi) administering a duplicate dose to the same individual, among others. Accordingly, devices have been developed in an attempt to mitigate and overcome some of the potential malfunctions of using needle injection, for example, by using intranasal administration.

Intranasal administration allows the introduction of medicament directly into the mucosal immune system via the mucosal tissue. Such intranasal medicaments can be administered using spray applicators, which administer the medicament in the form of small droplets. This form of delivery facilitates the development of both cellular and humoral immune reactions, and therefore protection from disease.

Some live virus vaccines are too pathogenic for use as immunogens, and vaccinations with inactivated viruses have the potential to be less effective and produce undesirable side effects, such as inflammatory reactions at the site of the injection. Such vaccines can be delivered intranasally by the attachment of an antigen to the mucosal surface of an animal. The attachment of an antigen to the mucosal surface can depend on particle size, the depth the antigen penetrates the mucosal tissue, and the distance travelled into the nasal cone. It has further been shown that a local antibody system and an interferon production mechanism operate at the primary site of infection in the nasal passage membranes (see e.g., U.S. Pat. No. 4,132,775). As such, intranasal administration of vaccinations has become a preferred route of administration for both inactivated viruses and attenuated live vaccines.

Some prior art devices have been developed that attempt to address intranasal administration. For example, U.S. Pat. No. 5,053,022 discloses an intranasal vaccination device for a horse comprising a tapered hollow flexible tube long enough to reach the tonsillar tissue of the horse and adapted to receive a syringe and a blocking device that allows the flexible device to pass through the blocking device until the wider portion of the taper is reached.

WO 2001/021151 discloses administering a one-dose, non-live influenza virus antigen using an intranasal delivery device that comprises a tip having spiral channels that result in the production of a spray when pressure is exerted on the plunger.

U.S. Pat. No. 7,296,566 discloses a syringe having a spray nozzle for delivery of liquid substances to a nasal passage. U.S. Pat. No. 8,499,721 discloses an intranasal vaccination device for birds comprising a beak receiving void into which the beak of a bird is disposed to receive fluid from fluid passages connected to the beak receiving void.

WI 2010/060462 discloses an apparatus for nasal administration of a pharmaceutical composition comprising a cannula for insertion into the nasal cavity of an animal.

However, these other known nasal delivery devices suffer from various disadvantages. For example, many are stationary, require cumbersome operation, single-dose capability, etc. The anatomical variation in the length of the nasal passage between animal species can require that different nozzle sizes and lengths be used depending on species or animal size. Additionally, cannulae and other insertion devices can generate excess physical stimulation of the nasal passage. This can damage the nasal mucosae and cause infection, in addition to causing inadvertent movement of the animal (which can lead to injury of either the animal or operator). Yet another disadvantage of known devices is the amount of dose that can remain in the device after administration (also known as a "dead volume"). This "dead volume" makes it difficult to determine the medicament dose that was actually administered to the animal.

Accordingly, there is a continuing need for improved injector devices and methods for their use, such as devices for injecting a large number of animals quickly and effectively.

SUMMARY

Described herein are embodiments of an improved intranasal administration device for intranasally administering one or more medicaments to a patient (e.g., swine, poultry, fish, sheep, goats, equids, cattle, dogs, cats etc.). The administration device can be used to administer medicament to a large number of animals in a quick and efficient manner to prevent and/or reduce operator error, operator fatigue, and injection malfunction.

Accordingly, in some embodiments, an intranasal administration device includes a hand-held portion comprising a gripping portion held by an operator and a spray head comprising a spray apparatus and a nozzle, a control unit coupled to the hand-held unit via at least one connecting tube, and one or more containers for holding medicaments fluidly coupled to the control unit. The control unit can comprise one or more pumps. The at least one connecting tube can be flexible enough to enable easy maneuvering of the hand-held unit and rigid enough to prevent widening of the tube due to inner pressure when medicaments pass from the containers to the hand-held unit.

In a representative embodiment, an intranasal administration device can comprise a spray head having a single spray apparatus and nozzle, and one or more dosing chambers fluidly coupled to the spray apparatus. In some embodiments, the administration device can further comprise one or more medicament containers, each medicament container being coupled to a respective dosing chamber. In some embodiments, one or more flexible connecting tubes can be used to couple the dosing chambers and the medicament containers, and the flexible connecting tubes can be configured to resist widening when medicament passes through them.

In another representative embodiment, an intranasal administration device can comprise a spray head having a first spray apparatus fluidly coupled to a first nozzle, and a second spray apparatus fluidly coupled to a second nozzle. The first spray apparatus and first nozzle can be movable relative to the second spray apparatus and second spray nozzle such that the distance between them can be varied depending on the anatomical considerations of a patient. In some embodiments, the first spray apparatus can be fluidly coupled to a first dosing chamber, and the second spray apparatus can be fluidly coupled to a second dosing chamber. In other embodiments, both the first and second spray apparatus can be coupled to a single dosing chamber. In some embodiments, the administration device can further comprise two or more medicament containers, each medicament container being coupled to a respective dosing chamber. In some embodiments, each dosing chamber is coupled to a respective pump configured to pump medicament from the dosing chamber to the spray apparatus.

In some embodiments, the administration device is configured to administer a single medicament. In other embodiments, the administration device is configured to administer a plurality of medicaments. In some embodiments, the medicament is administered via manual actuation of the administration device (e.g., by pulling a trigger). In other embodiments, the medicament can be administered automatically upon insertion of the spray head to a selected depth within the nasal cavity of a patient.

In another representative embodiment, an intranasal administration device can comprise: a hand-held unit comprising a gripping portion, a spray head having a spray apparatus, and a nozzle; one or more dosing chambers fluidly coupled to the spray apparatus; a control unit coupled to one or more medicament containers; at least one flexible connecting tube fluidly coupling the hand-held unit and the control unit, the flexible connecting tube configured to resist widening upon passage of the medicament therethrough; at least one pump configured to pump medicament from the control unit to the hand-held unit; one or more temperature control units operatively coupled to the medicament containers; one or more control panels configured to determine and display information relating to an administration process and to optionally transmit real-time data to a remote device; and a malfunction-identification device configured to identify malfunction of the administration device.

The foregoing and other objects, features, and advantages of the disclosure will become more apparent from the following detailed description, which proceeds with reference to the accompanying figures.

BRIEF DESCRIPTION OF THE DRAWINGS

FIG. 1 is a perspective view of a hand-held unit of an exemplary intranasal administration device.

FIG. 2 is a perspective view of a control unit of an exemplary intranasal administration device.

FIG. 3 is a perspective view of a medicament container of an exemplary intranasal administration device.

FIGS. 7-8 are exploded views of the tip portion of the hand-held unit of FIG. 4.

FIG. 9 is a perspective view of a control unit of an exemplary intranasal administration device.

FIG. 10 is a partial, exploded perspective view of the control unit of FIG. 9 with the side panel removed to show the valve assembly.

DETAILED DESCRIPTION

I. Definitions

Figure 4:
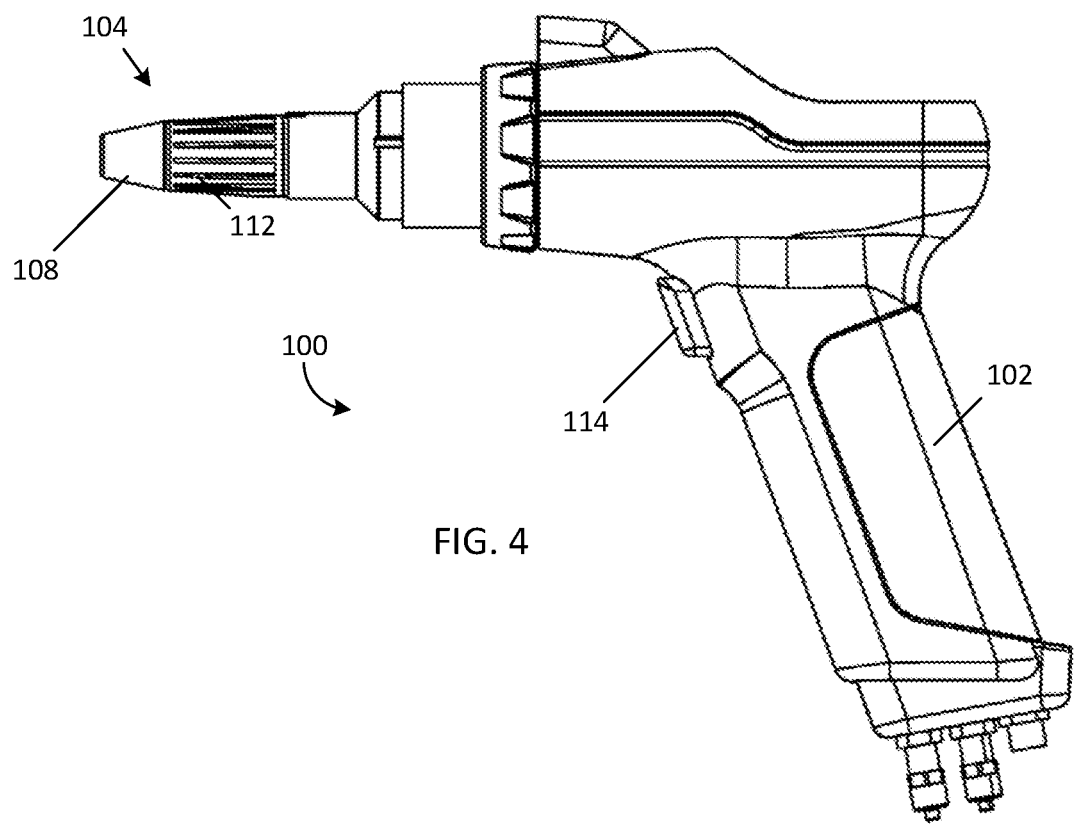
FIG. 4 is an elevational side view of a hand-held unit of an exemplary intranasal administration device.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

As used herein, the term "proximal" refers to a position, direction, or portion of a device that is closer to the user and further away from the administration site. As used herein, the term "distal" refers to a position, direction, or portion of a device that is further away from the user and closer to the administration site. Thus, for example, proximal motion of a device is motion of the device away from the administration site and toward the user (e.g., away from the patient's body), while distal motion of the device is motion of the device away from the user and toward the administration site (e.g., into the patient's body). The terms "longitudinal" and "axial" refer to an axis extending in the proximal and distal directions, unless otherwise expressly defined.

In the description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

As used herein, the term "approximately" means the listed value and any value that is within 10% of the listed value. For example, "approximately 100 degrees" means any value between 90-110 degrees, inclusive.

The term "medicament" as used herein refers to any material that needs to be administered to a patient, and includes, e.g., antibiotics, vaccines, hormones, food supplements, oils, vitamins, minerals, etc. In some embodiments, the medicaments are in liquid form. In other embodiments, the medicaments may be in powdered form and may be mixed with one or more solvents within the two or more containers or prior to being disposed therein.

II. Exemplary Embodiments

Disclosed herein are embodiments of an intranasal administration device usable to administer one or more medicaments to a patient intranasally, and methods for using the same.

Intranasal administration devices enable the administration of a desired dose of medicament to a patient. A dose may be any desired amount of a medicament or desired amount of a combination of medicaments and is not necessarily required to be used to treat the patient. Exemplary medicaments may include prophylactic compositions, such as vaccines, therapeutic compositions such as drugs, and/or other compositions which are of research or medicinal interest, such as proteins, nucleic acids, immunogens, live or inactivated viruses, reassortant live viruses, cold-adapted live viruses, attenuated live viruses, and/or adjuvants. A medicament may also be or comprise other substances which are useful for delivery or effectiveness. In some embodiments, the medicament can comprise species-specific compositions, such as cold-adapted live equine influenza viruses, that: (i) replicate only within a certain temperature range; (ii) do not form plaques in tissue culture cells; and/or (iii) have a certain phenotype.

The advantages of intranasal administration of medicaments include: a direct route to the blood stream; avoidance of hepatic first pass metabolism; bioavailability; ease and convenience of administration; and proximity to the central nervous system. Many types of medicaments can be delivered intranasally, including, but not limited to: topical anesthetics, sedatives, hypnotics, analgesics, ketamines, opiates, glucagons, vaccines, anti-nausea and motion sickness medications, antihistamines, antihypertensive drugs, psychoactive medications, antibiotics, and hormones.

FIGS. 1-3 illustrate components of an exemplary intranasal administration device. In certain embodiments, the intranasal administration device is useful for administering medicaments (including prophylactics and/or therapeutics) to a variety of animals. Components of the device (e.g., the nozzle) can be sized up or down for use with differently sized patients, including immature, young, or infantile animals.

Certain disclosed embodiments comprise: (a) a hand-held unit 100, a base or control unit 200 associated with the hand-held unit by at least one connecting tube 202 (see e.g., FIG. 15), and at least one container 300 removably attachable to the control unit 200 and/or the hand-held unit 100, or connected thereto by one or more connecting tubes. The one or more connecting tubes 202 can be sufficiently flexible to allow a user to maneuver the hand-held unit 100 and the control unit 200 and rigid enough to prevent widening of the connecting tube due to inner pressure when passing medicaments from the container 300 or the control unit 200 to the hand-held unit. Widening of the tube can cause inaccurate dosing of medicament. Further details of the flexible connecting tubes can be found, at least, in WO 2018/203203, which is incorporated by reference herein in its entirety.

In some embodiments, the control unit 200 can be configured to be worn by a user, such as on a belt, in waist bag, a vest, or in a carryon bag. In such embodiments, the connecting tube 202 can be flexible enough to allow the user to move the hand-held unit 100 in any direction, long enough to allow the user to fully extend his/her arm holding the hand-held unit 100, and rigid enough (i.e., non-expandable and non-deformable) to prevent widening of the tube due to pressure caused by medicament passing through the tube. Pressure changes have the potential to deform a tube that lacks sufficient rigidity during an administration of medicament, which can lead to inaccurate dosing of the medicament or a delay between the pump action and the administrating of the medicament to the animal. In some embodiments, the connecting tube can flex in all directions and can withstand twisting. In some embodiments, the connecting tube can elastically return to its original shape after being bent, twisted, extended, or otherwise deformed. For example, the tube can have an outer diameter of generally from about 1 mm to 10 mm, and more typically from about 4 mm to 5 mm in size. The internal diameter can be generally from about 1 mm to 5 mm, and more typically from about 2 mm to 3 mm. In some embodiments, the tube can be formed from polyamide. In some embodiments, the tube can further comprise a spring that allows the tube to have flexibility in all directions while resisting expansion of the tube. The spring can be external to the tube, internal to the tube, and/or formed integrally with the tube.

In some embodiments, the rigidity of the connecting tube is achieved by using a casing in conjunction with an elastic tube. In some embodiments, the casing can be formed separately and either wrapped around the elastic tube or placed inside the tube. In other embodiments, the casing can be formed integrally with the tube. In still other embodiments, the elastic tube can be formed of a material having a rigidity capable of withstanding the forces applied by the internal passage of fluids.

In some embodiments, the connecting tube 202 can be fabricated by laser cutting stainless steel to create integral links having a design that allows the tube to be flexible, while preventing radial expansion of the tube. Once laser cut, the resulting laser-cut steel tube is either mounted onto a flexible tube made of polymeric or elastomeric material, or coated with such a material.

Figure 5:
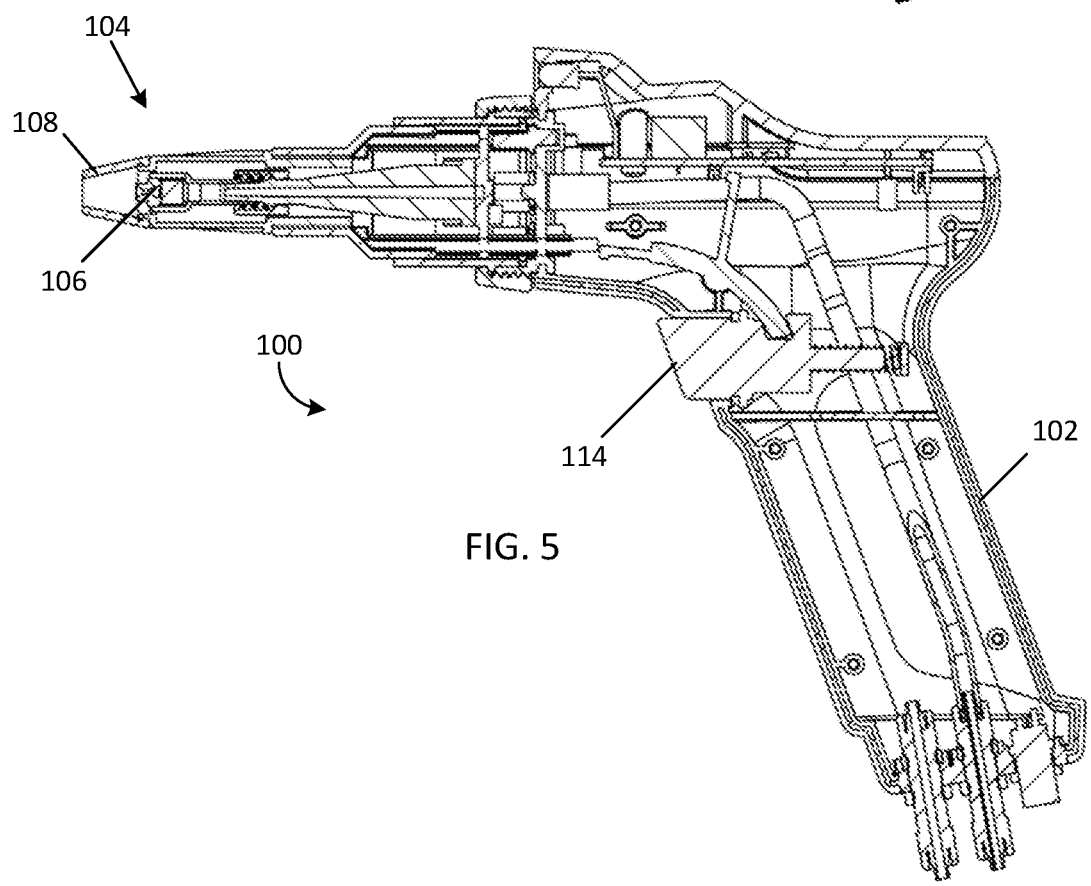
FIG. 5 is a cross-sectional view of the hand-held unit of FIG. 4.

Referring now to FIGS. 4 and 5, the hand-held unit 100 comprises a gripping portion 102 for being held by an operator and a spray head 104 comprising a spray apparatus 106 and a nozzle 108. The spray apparatus 106 can have any suitable shape, such as a straight or curved shape. In some embodiments, the spray apparatus 106 can be stationary with respect to the gripping portion 102. In other embodiments, the spray apparatus 104 can be movable and/or retractable with respect to the gripping portion 102. In such embodiments, urging the spray apparatus rearwardly (e.g., by pressing the nozzle 108 into the nostril of a patient), triggers the release of a predetermined dose of medicament into the patient's mucosal tissue. In some embodiments, as shown in FIGS. 6-8, the spray apparatus 106 can be coupled to the hand-held unit using a luer lock 110.

Figure 6:
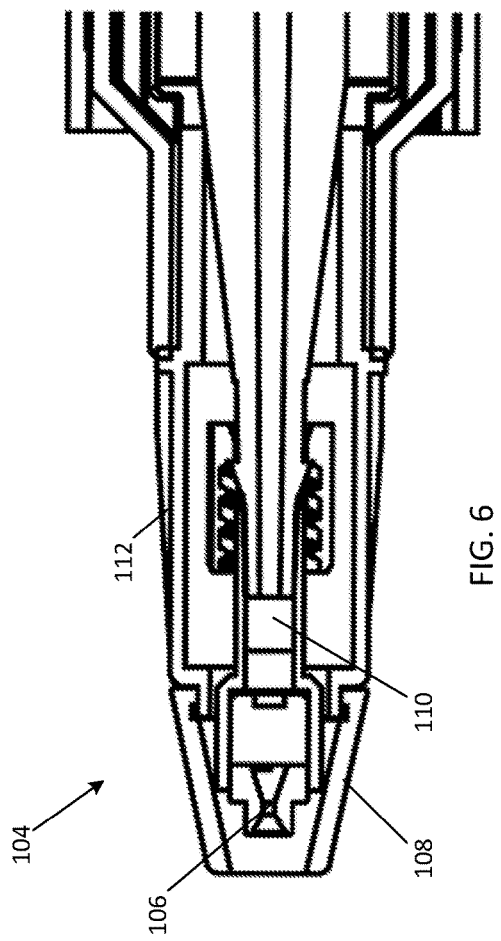
FIG. 6 is an enlarged, cross-sectional view of the tip portion of the hand-held unit of FIG. 4.
Figure 7:
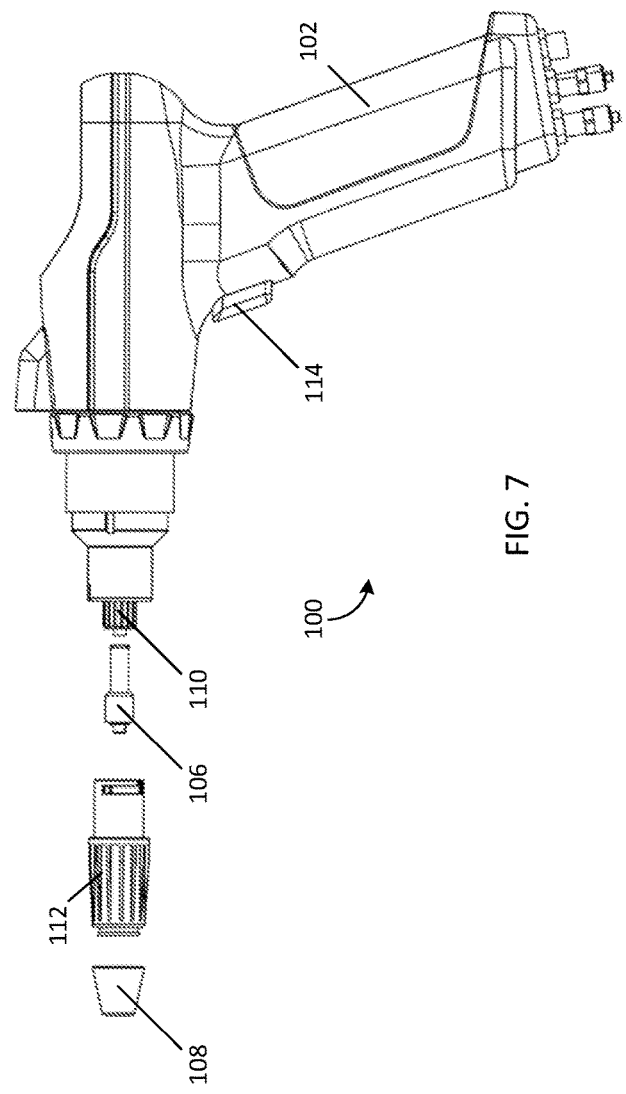

Referring still to FIGS. 6-8, as noted above, the spray head 104 can comprise a nozzle 108 for insertion into the nostril of a patient. The nozzle 108 can comprise silicone, rubber, or thermoplastic material and can be configured to: (i) fit and seal the nostril of the patient; (ii) prevent dispersion of medicament outside the nostril; and (iii) direct the spray through the nostril toward the inner tissue, thereby ensuring maximal mucosal exposure.

The external shape of the nozzle 108 can vary substantially depending on the medicament to be administered and on the anatomical considerations of the patient, and may include, for example, cylindrical or conical configurations. The illustrated embodiments show a conical nozzle; however, in other embodiments the nozzle 108 can have a substantially uniform cylindrical exterior. The length of the nozzle 108 can vary depending on the location of the target administration site. For administering a dose to animals with longer and narrower nasal passages, the nozzle can have a cylindrical exterior surface having a radius in the range of about 1.0 millimeters to about 10 millimeters, and a longitudinal length in the range of about 70 millimeters to about 180 millimeters.

Figure 19:
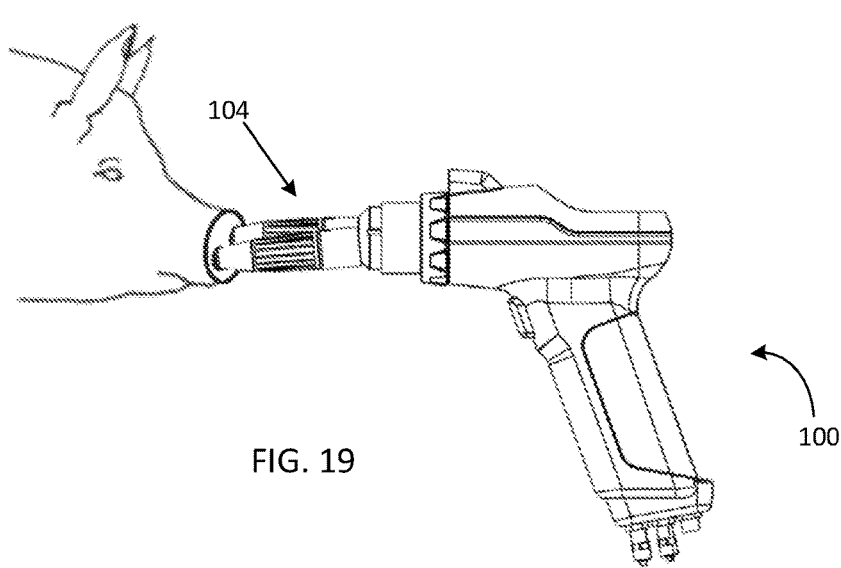
FIG. 19 is an elevational side view of a hand-held unit of an exemplary intranasal device being used to administer medicament intranasally to an animal.

In some embodiments (see e.g., FIG. 19), the spray head 104 of the intranasal administration device can comprise two spray apparatuses, each coupled to a nozzle configured to: (i) fit the animal's nostril; (ii) prevent dispersion of the spray outside the nostril; and (iii) direct the spray through the nostril towards the inner mucosal tissue. The distance between the two spray apparatuses and therefore between the two nozzles can be adjustable such that it can be varied depending on the distance between the nostrils of the animal, thereby ensuring maximal mucosal exposure and contact with the sprayed medicament. In specific embodiments, the intranasal administration device is configured to administer a different medicament through each nozzle. As discussed in more detail below, embodiments of the spray head are configured to be removable such that they can be replaced. For example, a two-nozzle spray head can be replaced with a single nozzle spray head for use with selected animals.

The spray head 104, the spray nozzle 108, and/or the spray apparatus 106 can be made from a flexible material or a substantially rigid material depending on the selected application or anatomical considerations of the selected patient species. For example, a substantially rigid material may be selected for use with bovine animals which may have a relatively short and uncomplicated intranasal passages to traverse to deliver the dose to the target or dose-location coordinate. Alternately, a more flexible spray head, spray nozzle, and/or spray apparatus may be selected for use with equids which have longer intranasal passages and which may also have a blind-ending nasal passage (such as a nasal diverticulum), which may have to be worked around to deliver a dose to the desired target or dose location-coordinate.

The spray head 104 (including spray nozzle 108, and/or spray apparatus 106) can comprise materials that are compatible with the medicament to be administered and which will not degrade such that the medicament will not be altered by heat, light, ultraviolet radiation, etc. For example, the spray head can comprise glass, polymeric materials, such as polyethylene, polypropylene, polyurethane, polyvinyl chloride, rubber, silicone, and/or metals or alloys.

In some embodiments, as shown in FIG. 8, the spray head 104 can further comprise a movable head 112 that covers the spray apparatus 106. The movable head 112 can be movable between an extended position and a retracted position. In some embodiments, movement of the movable head 112 to the retracted position enables passage of medicament through the spray apparatus 106 (e.g., by opening a valve associated with the spray apparatus). In such embodiments, urging the movable head 112 rearwardly (e.g., by pressing it into the nostril of a patient), triggers the release of a predetermined dose of medicament into the patient's mucosal tissue. In some embodiments, the entire spray head 104, including the movable head 112, spray apparatus 106, and nozzle 108, is a detachable and replaceable unit that can be coupled to the hand-held unit 100.

In some embodiments, the minimum dosage can be from about 1 mL to about 1.5 mL. In some embodiments, the minimum dosage can be "chased" through the intranasal administration device using a dose propellant.

Generally, the medicaments are administered in a liquid form (e.g., as a spray). In some embodiments, the containers 300 are provided with a ready-for-use liquid medicament. In other embodiments, the medicament to be administered is administered in a dry form (e.g., as a sprayed powder). In such embodiments the medicament is held within the containers in a dry form. In still other embodiments, the containers 300 are provided with a medicament (e.g., in a dried or powdered form) that needs to be processed or prepared prior to use (e.g. by the addition of water or other solvent thereto). Accordingly, in some embodiments, the containers 300 can be internally divided into two or more compartments for holding one or more powdered medicaments and one or more solvents. Prior to administration of the medicament(s) the one or more solvents can be admixed with the powder to create the ready-for-use medicament.

In some embodiments, the containers 300 can be formed separately and can be removably couplable to the control unit 200. In such embodiments, the containers can either be refilled or replaced with full containers when emptied. In other embodiments, the containers 300 can be formed integrally as part of the hand-held unit 100, the control unit 200, or both, and can be refilled with a suitable liquid medicament when emptied. In some embodiments, the containers 300 can be made of rigid material (e.g., a metal or a rigid polymeric material). In other embodiments, the containers 300 can be made of flexible material (e.g. a plastic bag or a flexible polymeric material). In some embodiments, the containers 300 can be transparent or substantially transparent, thus allowing a user to see the content and the level of content within. In other embodiments, the containers 300 can be opaque, for example, when the medicament(s) they hold are light-sensitive.

In some embodiments, each medicament can be administered by manual actuation of the intranasal device, for example, by manually pressing and/or pulling a trigger 114 located on the gripping portion 102 of the hand-held unit 100. Suitable triggers 114 can be a lever or button. In such embodiments, each press of the trigger 114 will actuate a motor of the device to administer a predetermined amount of the medicament to be administered. In some embodiments, the device can be configured to sequentially deliver doses of two or more different medicaments. In such embodiments, a first press of the trigger will administer a selected dose of a first medicament, and a second press of the trigger will administer a selected dose of a second medicament.

In other embodiments, each dose can be administered automatically (e.g., without pressing the trigger). In such embodiments, the spray head 104 of the hand-held unit 100 can additionally comprise means, such as a measurement device or contact sensor, for identifying that the spray head 104 (e.g., the nozzle 108 of the spray head) has reached a selected location (e.g., depth) within the nasal cavity of the patient. Once the spray head 104 has reached the selected location, the control unit 200 can activate a pump 204 (see e.g., FIG. 11) configured to deliver a predetermined dosage of medicament through the hand-held 100 and into the patient.

Notably, animals of different sizes may all require administration of medicament. This can require spray heads 104 of differing types, shapes, and sizes. Accordingly, in certain embodiments, the intranasal administration device is configured allow for the replacement of spray heads (e.g., replacing the nozzle or the spray apparatus) for maintenance, preventing contamination delivery between the individuals, and/or for adjusting the type and size thereof. In certain embodiments, the entire spray head 104 of the hand-held unit is replaceable, allowing a user to quickly and easily switch between spray nozzle types, e.g. between nozzles of different lengths and/or widths, between stationary and movable nozzles, and/or for replacing damaged nozzles.

In certain embodiments, the intranasal administration device is configured to allow a user to control and/or adjust the spread of the spray (distance and diameter) according to the anatomy of the animal being treated and/or vaccinated, as described in more detail below.

The size of the spray droplets may be adjusted to beneficially affect delivery of a medicament in terms of medicament absorbance in the mucosal membrane. Accordingly, in certain embodiments, the intranasal administration device further comprises a mechanism for controlling and/or adjusting the size of the spray droplets. In some embodiments, this spray droplet adjustment can be achieved by adjusting the pressure applied by the pump or the motor using a pulse-width modulation (PWM) controller. This allows differently sized droplets to be used on animals of different sizes and ages, for example, using smaller droplets on smaller and/or younger animals. In addition, this allows for the adjustment of droplet size for different medicaments and/or vaccination components having different viscosity, which can influence the size of the created droplets.

Particle sizes can affect the amount and rate of medicament absorption. Particles of medicament having a diameter of less than about 1 µm can remain suspended during administration, as the time required for the particle to diffuse to an airway wall tends to be greater than the time to complete the inspiratory phase of a normal breath. Deposition of medicament in the lung may be facilitated using particles having a diameter of approximately 3 µm. Larger particles having a diameter of greater than approximately 5 µm are often deposited in the upper airways. Accordingly, in certain embodiments, the intranasal administration device can be configured to generate droplets of medicament that are between greater than 0 µm and approximately 250 µm in size. In some embodiments, the intranasal administration device is designed to deliver a dose of about 0.25 ml to about 2 ml of medicament to each animal, in each spraying process.

Figure 11:
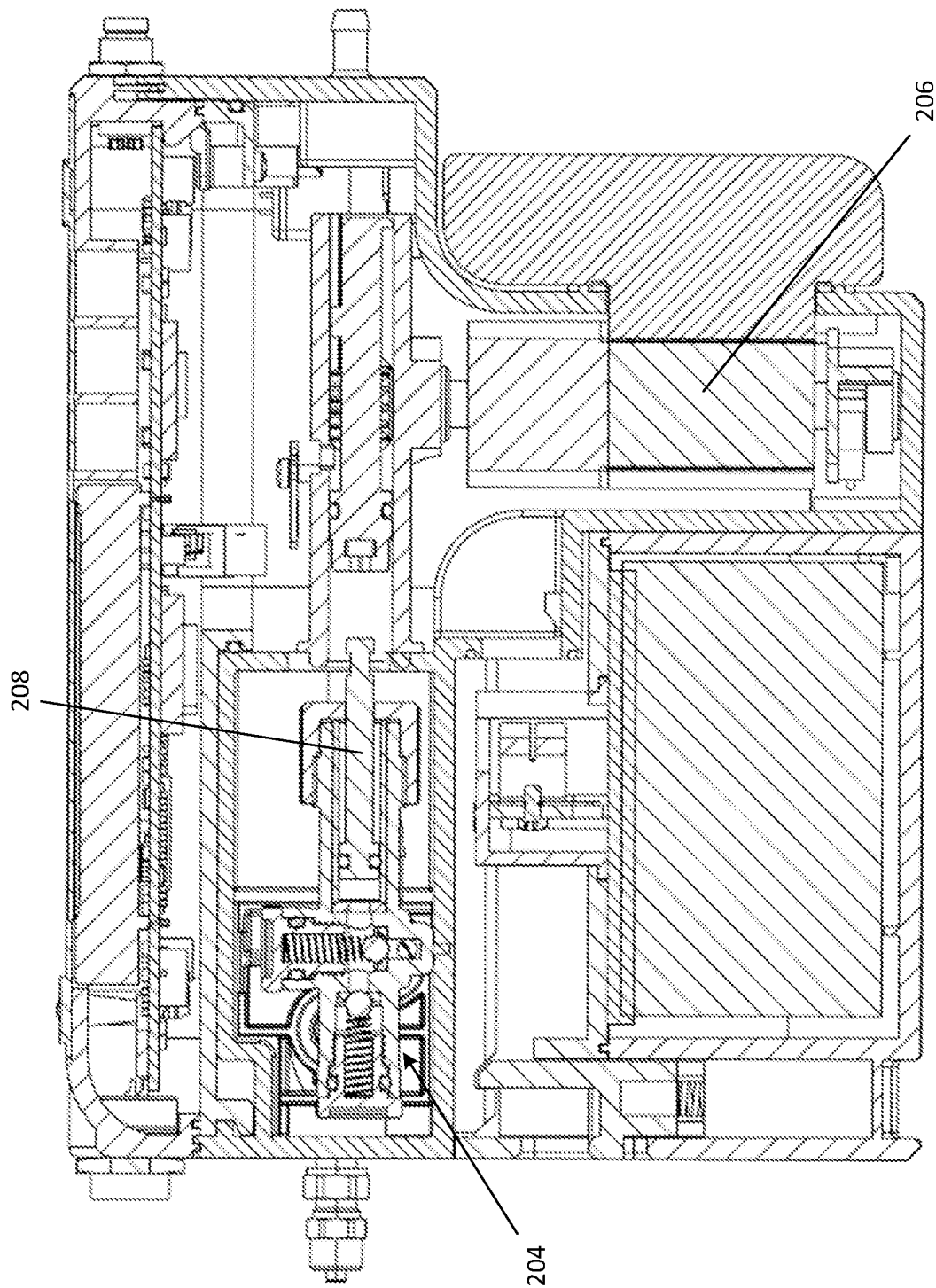
FIG. 11 is a cross-sectional side view of the control unit of FIG. 9.

The intranasal administration device can further comprise means for delivering a medicament from its respective container 300 to the hand-held unit 100 and into the patient's nostril(s). Referring to FIG. 11, in some embodiments, the control unit 200 comprises a pump 204. The pump 204 can be actuated by one or more motors 206 which can rotate one or more drive shafts 208 coupled to the pumps. The pump 204 can be a piston or plunger pump. The pump 204 can be fluidly coupled to one or more containers 300 and can be configured to pull and/or push the same or different predetermined amounts of medicament from each container 300 and deliver the same to the hand-held unit 100 and thereby to the spray head 104. The predetermined amounts of each medicament can be equal or different depending on the type of medicament to be administered. The intranasal administration device can further comprise one or more motors designed to operate the various components of the apparatus, such as the one or more pumps.

In some embodiments, the intranasal administration device can comprise two or more pumps 204 located at the control unit 200, wherein the number of pumps is identical to the number of containers 300, and wherein each pump 204 is coupled to a discrete container 300. In this configuration, each pump 204 is designed to pull and/or push a predetermined amount of medicament from its respective container 300 and to sequentially deliver the medicament to the spray head 104 in the hand-held unit 100 and into the patient according to a predefined administration order.

In some embodiments, the intranasal administration device can be configured to be suitable for remote locations with limited power supply. In other embodiments, the intranasal administration device may be configured to be operated electrically. In some embodiments, the intranasal administration device can further comprise a power source located at, for example, the control unit 200, the hand-held unit 100, or both. In some embodiments, the power source can be positioned as a separate power source unit electrically connected to the administration device. In some embodiments, the power source is rechargeable. In other embodiments, the power source can be disposable (e.g., disposable batteries). In some embodiments, the administration device further comprises a power-meter configured to display the amount of electricity remaining and/or send an alert when the power reaches a selected level that can interfere with the operation of the administration device.

In some embodiments, the intranasal administration device can further comprise an administration indicator configured to electrically actuate the valves and/or the one or more pumps 204. For example, in embodiments comprising a single pump, after medicament A is administered, the administration indicator can close a valve positioned at the medicament exit of container A and open a valve positioned at the medicament exit of container B. Thus, when the pump is activated, it can draw medicament only from container B, which has a valve in the open position. Alternatively, in embodiments comprising two or more pumps wherein each pump is associated with a discrete container 300, after administering medicament A, the administration indicator can turn off pump A associated with container A and activate pump B associated with second container B. Thus, the pumps can be activated according to the order of administration. The administration indicator can furthermore be configured to signal (e.g., visually, auditorily, and/or in a tactile manner such as by vibration) that a medicament has been administered and indicate that the next medicament is ready to be administered.

In certain embodiments, the intranasal administration device further comprises a dosing chamber associated with each container 300 for holding a medicament, and a piston for pushing/pulling the medicament out of said dosing chamber, and wherein a medicament is loaded automatically into the dosing chamber right after delivering of a dose of medicament to the animal. In a specific embodiment, there is a single dosing chamber located at the hand-held unit 100, which receives a different medicament before each delivery according to a desired order of delivery. In an alternative embodiment, there are several dosing chambers each fluidly coupled to an associated container 300, and each dosing chamber is filled with a single type of medicament which is then delivered to the spray head 104 according to the order of delivery. Further details of exemplary dosing chambers can be found, at least, in WO 2018/203203.

In certain embodiments, the amount of medicament administered is controlled by an encoder. In some embodiments, the encoder can be coupled to the driving shaft or piston 208 of the pump 204 (e.g., located on the hand-held portion or the control portion). The encoder is configured to, by sensing the amount of rotation of the motor, set the position of the piston head to enable administration of a predetermined amount of medicament. This function is useful to set different medicament volumes to be administered. The dose volume can be determined for each patient or class of patients, but for certain embodiments typically varies from greater than 0 milliliters to about 10 milliliters, and more typically from 0.05 milliliters to 5 milliliters.

In some embodiments, the intranasal administration device further comprises a control panel. The control panel can be configured to display desired information related to an administration process to a user and enable him or her to control various functions of the administration process. The control panel can optionally transmit real-time information to a remote device, thus allowing for data storage and/or remote control of the device. In some embodiments, the control panel can control, for example, the amount of each medicament to be administered and/or the administration order of the different medicaments. The control panel can display information such as, for example, the amount of remaining medicament in each container and/or the number of patients that have received medicament, the overall time spent on administration, information regarding the rotation of the motor, etc. As shown in FIG. 2, in some embodiments, the control panel 210 is located on the control unit 200. In other embodiments, the control panel can be located on the hand-held unit 100.

In certain embodiments, the intranasal administration device further comprises a volume control apparatus for setting and verifying different volumes of a dose to be administered. In some embodiments, the volume control apparatus can comprise, for example, an encoder, an electrical meter, sensors and indicators for measuring medicament amounts. In other embodiments, the volume control apparatus can comprise a simple fixed piston and plunger that can be adjusted (e.g., manually or electrically) to deliver various amounts.

In some embodiments, each container 300 can comprise a valve actuatable between an open configuration and a closed configuration. In the open configuration, medicament can pass through the valve and in the closed configuration medicament is prevented from passing through the valve. For example, in the open configuration medicament can pass from the container 300 to the control unit 200, and in the closed configuration medicament is prevented from passing from the container 300 to the control unit 200. In some embodiments, the valves are non-return or check valves which allow passage of medicament therethrough in only a single direction. In other embodiments, the valves can be configured such that they can be actuated electrically (e.g., by a microprocessor) between the open and closed configurations. In still other embodiments, the valves can be configured such that they can be actuated manually (e.g., by pressing a button, flipping a switch, or turning a lever). The valves can be configured to allow fluid flow in only one direction (e.g., from the container into the dosing chamber) thus preventing the backflow of medicament into the container, thereby preventing contamination of the containers and extending the shelf life of said containers, so that they can be re-used if an amount of medicament remains following the administration procedure.

Figure 13:
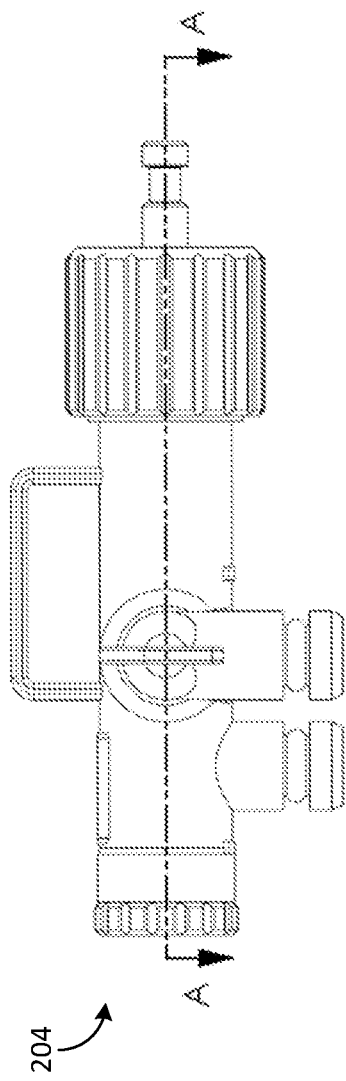
FIG. 13 is an elevational side view of the valve assembly of claim 12.
Figure 12:
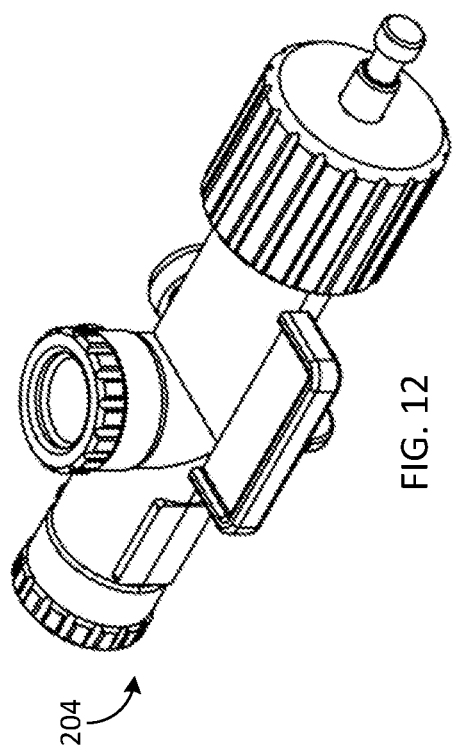
FIG. 12 is a perspective view of a valve assembly of an exemplary intranasal administration device.
Figure 14:
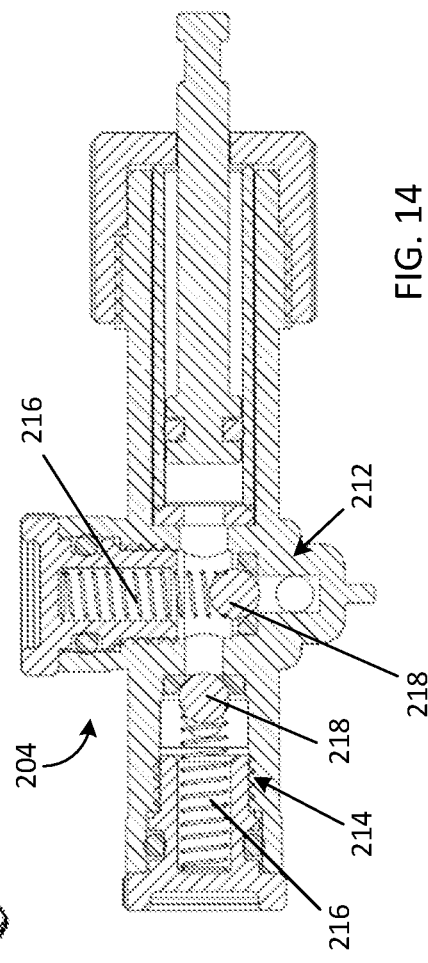
FIG. 14 is a cross-sectional side view along the line A-A shown in FIG. 13.
Figure 15:
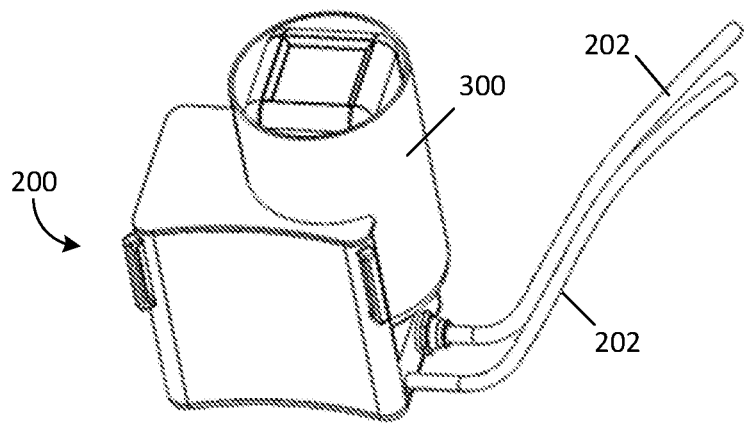
FIGS. 15-16 are perspective views of a control unit of an exemplary intranasal administration device.
Figure 16:
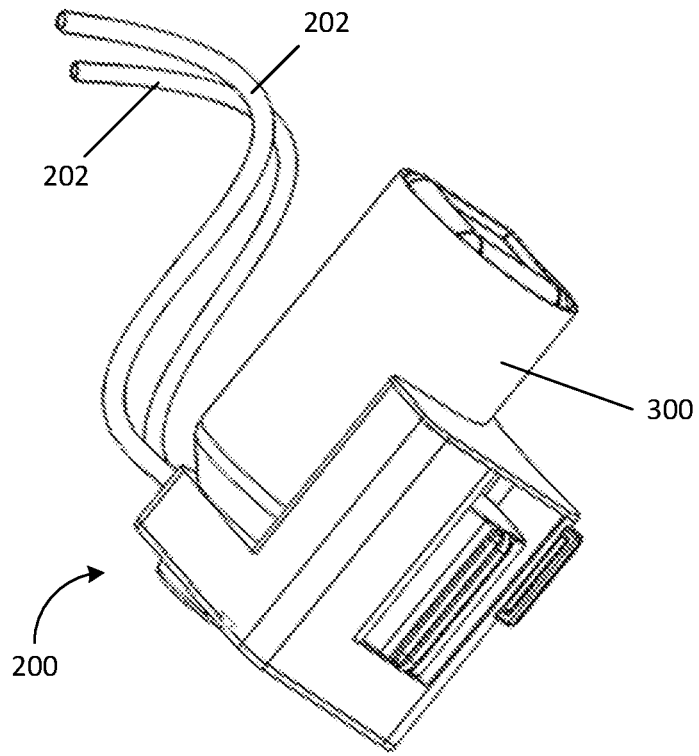
Figure 17:
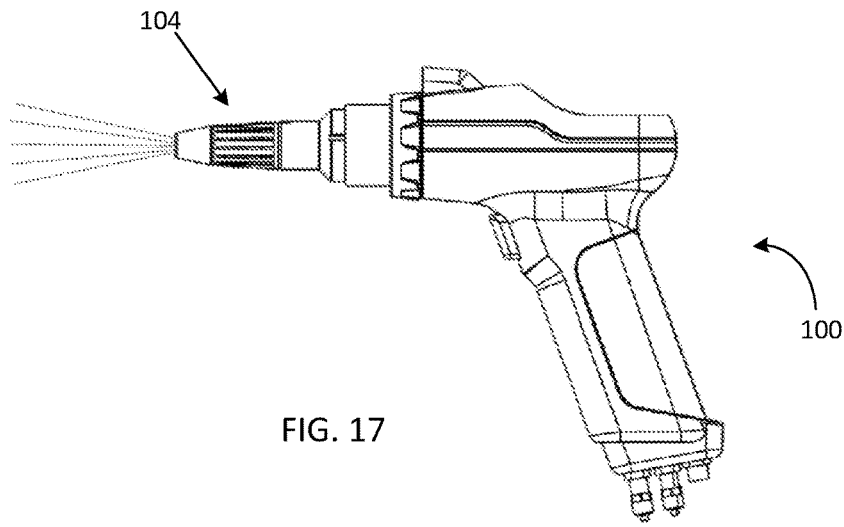
FIG. 17 is an elevational side view of the hand-held unit of an exemplary intranasal administration device.
Figure 18:
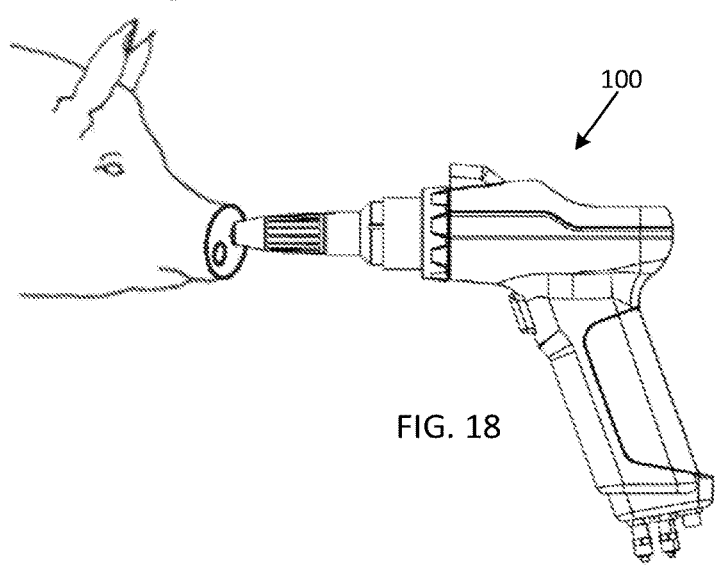
FIG. 18 is an elevational side of view of the hand-held unit of FIG. 17 being used to administer medicament intranasally to an animal.

Referring now to FIGS. 12-14, the intranasal administration device can comprise two or more non-return valves (e.g., check valves, inlet non-return valves, lift-check valves, etc.) located, for example, in pump 204 of the control unit 200. In some embodiments, the valves are non-return or check valves which allow passage of medicament therethrough in only a single direction. For example, a first check valve 212 can allow the passage of medicament from the container 300 to the control unit 200 but prevent backflow from the control unit 200 to the container 300, and a second check valve 214 can allow the passage of medicament from the control unit 200 to the hand-held unit 100 but prevent backflow from the hand-held unit 100 to the control unit 200. The particular embodiment of FIGS. 12-14 includes valves 212, 214 each comprising a spring 216 and a stopper 218 (which can be any of various shapes including, for example, a sphere, a disk, a cone, etc.). The spring 216 exerts a biasing force against the stopper 218, biasing the valve into a closed position and preventing medicament from flowing through the valve. If the pressure external to the valve (e.g., in connecting tubes 202) is less that the opening (or "cracking") pressure of the check valve (e.g., less than the force exerted by spring 216), the valve remains closed. This can prevent fluid from the containers from flowing into the control unit 200 until the pump is activated to pressurize the fluid and/or prevent fluid from the control unit 200 from flowing into the hand-held unit 100. If the external pressure is greater than the cracking pressure of the check valve, medicament can push the stopper 218 against the spring 216, compressing the spring and allowing medicament to flow through the valve in one direction.

In other embodiments, the valves can be configured such that they can be actuated electrically (e.g., by a microprocessor) between the open and closed configurations. In still other embodiments, the valves can be configured such that they can be actuated manually (e.g., by pressing a button, flipping a switch, or turning a lever).

In some embodiments, an intranasal administration device can be configured to spray two or more medicaments into the nostril(s) of an animal, and can comprise: (i) a hand-held unit 100 having a gripping portion 102 for being held by an operator; (ii) a control unit 200 fluidly coupled to the hand-held unit 100 using two or more connecting tubes 202; (iii) two or more containers 300, respectively, each for holding a different medicament; (iv) a power source; (v) an administration indicator for identifying that a medicament has been administered in full and determining the next medicament to be administered; and (vi) a control panel for determining and displaying various functions of the administration process. Each container 300 can be removably coupled to the control unit 200. The administration device can further comprise two or more pumps 204. The medicaments can be administered sequentially or simultaneously.

In some embodiments, the intranasal administration device can be configured to administer two or more different medicaments into a patient. In specific embodiments, the intranasal administration device can comprise three main subsystems: (1) a hand-held unit 100 comprising a single or double spray nozzle, non-return valves, printed circuit board (PCB), and a screen; (2) a control unit comprising a motor, a pump, non-return valves, PCB, medicament containers, a position detector, a temperature detector, a pressure detector, an RFID scanner, a Bluetooth or any RF transmitter, and a power-supply (e.g. batteries); and (3) tubes and electrical wires connect the hand-held unit 100 and control-unit 200.

In certain embodiments, each vaccination element and/or medicament administered by the intranasal administration device is a solution or suspension, such as a water-based solution, a water-based suspension, an emulsion, or a solution comprising an organic solvent or suspension aid. In other embodiments, the medicament can comprise at least one antigen, live virus, attenuated virus, inactivated virus, conjugated antigen, conjugated virus, DNA, RNA, bacteria, yeast, or any combination thereof. In yet other embodiments, the medicament can comprise antibiotics, steroids, respiratory treatments, or any combination thereof.

In certain embodiments, each container 300 of the intranasal administration device further comprises an identification marker. The identification marker can be any suitable marker for conveying information (e.g., an RFID code, a QR-code, a barcode, a color sticker, etc). In some embodiments, the identification marker indicates, for example, the type of medicament within each container, the amount of medicament that needs to be administered from each container, the manufacturing date, and/or the expiration date. Accordingly, in some embodiments, the intranasal administration device further comprises a reader unit configured to read the identification markers and to transmit the data to the control unit and/or to a remote unit.

In some embodiments, the reader unit can be configured to emit and receive light. In such embodiments, the identification markers can be comprised of light absorbing materials and/or a light reflecting materials. For example, a first container can have a light-absorbing sticker (e.g., a black sticker) and a second container can comprise a light-reflecting sticker (e.g., a white sticker). When a container is coupled to the control unit, the reader unit can read the identification marker in order to distinguish between the first and second containers and determine the contents and/or required dosage for each container. The reader unit can then transmit that information to the control unit and/or a remote unit.

In some embodiments, each animal can be implanted with an RFID tag. The RFID tag of an animal can be scanned to prior to administration, to ensure that the animal has not already received the medicament. During or after the administration process the RFID tag of the animal can be logged and the data transmitted to a control system (e.g., a smartphone, a cloud-based data housing system, or a local server).

When administering medicament to a large number of animals, the user may need to hold the administration device for a long time. Accordingly, in certain embodiments, the weight of the hand-held unit 100 is configured to be as light as possible, for example, between about 150 to about 200 grams, such as 160 grams, 170 grams, 180 grams, or 190 grams.

In some embodiments, the intranasal administration device further comprises one or more heating units for heating the medicament to be administered. Pre-heating some medicaments to the approximate body temperature of the animal prior to administration can improve absorbance of the medicament. In some embodiments, each heating unit can be coupled to a respective container 300. In other embodiments, a heating unit can be positioned along a connecting tube 202, or within the hand-held unit 100. A temperature control unit used can be selected according to the system requirements. In some embodiments, the heat used to raise the temperature can be generated by the engine or motor of the intranasal administration device, and/or by a Peltier device or other thermoelectric cooling apparatus. This can reduce energy consumption, as well as improve cost and performance of the device.

In a specific embodiment, the intranasal administration device can be configured to meet any or all of the following requirements:

(1) The device can administer 3 L (approx. 2.55 kg) of medicament within a 6-hour timeframe. The operator is expected to carry 1 to 2 L of medicament and refill from a central location when required.
(2) The heating system has the capacity to heat 3 kg of medicament.
(3) The medicament is a protein in mineral oil emulsion with a specific heat capacity of 2130 J/kg. The medicament is to be heated to approximately 38° C. For example, if heating from about 28° C. to about 38° C., the total heat requirement is 54315 J or 0.15 kwh ($Q=2.55*2130*10$). In addition, the pumping energy and pump motor cooling should be considered, which could add an extra 40-50,000 J to the energy requirement.

(4) Assuming a 6 hour working day, the heating power required is 2.5 W ($P=54315/(6*3600)$). The spraying pump is also expected to add another about 3 W to the load, and therefore the overall power demand is about 5-6 W.

(5) The liquid temperature at spraying is within an accuracy of +/−1° C. of a preselected temperature.

(6) The total weight of the equipment including inoculant should not exceed 5 kg in weight and 5 L in volume.

(7) The heating system prevents overheating of the medicament by a thermocouple switch.

(8) The heating system is safe for the user.

In a specific embodiment, the intranasal administration device can comprise two main subsystems: (i) a medicament storage and heating system housed in a backpack or belt unit; and (ii) a hand-held unit which is fed therefrom. In such embodiments, the medicament is pumped through a heating device to bring it to the selected temperature and is then administered in precise dosages.

In some embodiments, a small Li-Ion battery can be used to power a Peltier device which supplies heat to or removes heat from the medicament until a desired temperature is reached. Notably, the system controls the temperature to prevent overheating of the medicament, which could, in some cases, render it unusable. In this way, the battery energy of the device can be used more efficiently since the batteries only need to supply a portion of the heating energy. Peltier devices work best when the "temperature lift" (e.g., the difference in temperature between the hot side and cold side) is kept to a minimum. For example, in some embodiments, the lift can be approximately 10° C. which is low enough to enable the Peltier to operate efficiently. In an exemplary embodiment, a Coefficient of Performance (COPh) of approximately 3 can be achieved thereby reducing the battery requirement to ⅓ of the battery energy required by a "battery only" system. In practical terms, this energy load could be realized by, for example, a Li-ion battery of around 50 g with dimensions of 50×50×10 mm, capacity 2500 mAH, and power 1.8-2 W.

In some embodiments, the Peltier device can be used in conjunction with waste heat from the motor of the intranasal administration device by capturing the waste heat and using it as additional heat input to the "cold side" of the Peltier device. In an exemplary motor, the efficiency can be around 60%, and therefore 1-2 W of heat can be generated in the motor body. This additional heat can be utilized by the Peltier device, and thus improve the overall heat pump performance as well as substantially reduce the battery energy budget.

Accordingly, in certain embodiments, the intranasal administration device comprises a heat generating unit which is based on a Peltier/pump motor assisted heating. The amount of medicament injected by the Peltier/pump motor assisted heating apparatus is critical. As such, the intranasal administration device may require calibration prior to an initial use, or prior to each use. Accordingly, in certain embodiments, the device further comprises an encoder for calibrating the location of the piston or the pump, to thereby obtain accurate calibration.

Many known intranasal apparatuses use manual calibration of the dosage to be administered, which can result in large deviations within the amount of medicament due to, for example, operator error and the inaccuracy of cylinder measuring techniques. In contrast, in some embodiments of the present device, the instant encoder can enable radial resolution of 5 degrees, which leads to a linear movement of as little as 0.0006 mm of the piston, and therefore provides high dosage precision. However, over time dosage deviations can occur due to manufacturing tolerances resulting in cylinder differences and/or certain degrees of freedom between moving mechanical parts that change due to corrosion and abrasion. Accordingly, in certain embodiments, each intranasal administration device can be calibrated during manufacturing and additionally calibrated by the end user according to need, prior to each use, or periodically.

Accordingly, in some embodiments, the intranasal administration device further comprises an automated calibration system that enables an end user to calibrate the intranasal device. In such embodiments, the automated calibration system may comprise a sealed container with electrodes at its bottom and top, wherein the dimensions of the container and therefore the distance between the electrodes is known. To calibrate the device, the user can turn the intranasal administration device to a "calibration mode" such that the device will administer (e.g., by spraying) a predetermined dose of a testing liquid (e.g. 1 cc of water) into the sealed container. Once the liquid reaches the top electrode, the calibration system notifies the device and stops the administration. The calibration system determines the number of doses that were required to fill the known volume of the container, calculates the volume of each dose, and compares it to the predetermined amount of each dose. This allows the calibration system to determine if there is any discrepancy in the dose amount and enables the calibration system to automatically calibrate the intranasal administration device in accordance with the measured discrepancy.

In certain embodiments, the intranasal administration device further comprises a control unit capable of identifying malfunctions in the administration procedure, such as partial dosing, clogging, air bubbles within the tubes, leakage, and/or emptying of the containers. The control unit can additionally identify malfunctions within the different components of the intranasal administration device, such as low power, faulty pump(s), torn tube(s), etc.

Incomplete dosing and other malfunctions can occur due to human error, (e.g., when a user withdraws the spray nozzle out of the patient's nasal passage before all the medicament has been administered), or due to mechanical malfunction (e.g., the piston not moving all the way forward within the dosing chamber to expel the medicament, clogging of the tubes or of the spray nozzle, for example, due to dirt or viscosity of the liquid, and air bubbles infiltrating the system which may alter the final volume of the injected medicament). Regardless of cause, incomplete administration results in the patient receiving only a portion of the intended dosage of medicament. These malfunctions may prevent the accurate administration of a medicament to the patient or prolong the duration of each administration.

In certain embodiments, the intranasal administration device further comprises a malfunction-identification system, which can be configured to identify the above described malfunctions, as well as others, and send an alert to the user. Such a malfunction-identification system can comprise various mechanisms, for example, a probe at the spray nozzle or spray nozzle head that identifies an early withdrawal of the device prior to the completion of the administration, a probe coupled to the dosing chamber that identifies whether the piston head moves all the way to the end of the dosing chamber, a probe at the piston head that identifies whether the head of the piston moves backwardly before the piston head moves all the way to the end of the dosing chamber (e.g., indicative of an incomplete administration), a sensor that identifies whether the piston does not move or moves very slowly (e.g. using the encoder and internal clock) which can be indicative of a clog, and/or a sensor that identifies whether the plunger moves too fast (e.g. using the encoder and internal clock) which can be indicative of an air bubble or leakage. The malfunction-identification system can further function to calculate the remaining amount of medicament in each container (e.g., by multiplying the number of doses by the administration dosage), measure the current used to activate the motor, which can correspond to the presence of an air bubble, leakage or a clog, etc. The malfunction-identification system can further be configured to measure the duration of each dose and/or the electric current used, wherein any additional duration and/or current used beyond a certain amount can indicate clogging within the system, and any decrease in duration and/or current used beyond a certain amount can indicate an air bubble or leak within the system, or the end of the medicament in the container.

In some embodiments, the intranasal administration device further comprises an unclogging procedure to remove clogs that may occur within the spray nozzle or the spray head. The unclogging procedure can comprise spraying water or other cleaning fluid through the clogged spray nozzle, the water or cleaning fluid being contained in a container connected in parallel to the hand-held unit, such that the unclogging procedure can be carried out as part of the administration procedure, without the need to stop and clean the device. For example, an exemplary intranasal administration device can comprise a hand-held unit fluidly coupled to a control unit which comprises two containers. One container can hold medicament, and the other can hold cleaning solution. In use, the intranasal administration device can be configured to alternate between doses of medicament and doses of cleaning fluid, such that a user can administer a dose of medicament to a patient, remove the spray nozzle from the patient, expel a dose of cleaning solution (e.g, onto the ground), and continue on to the next patient.

The above described embodiments of the intranasal administration device can be used in the following exemplary manner. The nozzle(s) of the spray head can be inserted into the nostril(s) of a patient. In some embodiments, the user can press the spray head into the patient's nostril(s), thereby triggering the administration of a dose of medicament. In other embodiments, the user can actuate a trigger, thereby administering a dose of medicament. The spray head can then be removed from the patient's nostril(s) and the user can continue on to the next patient.

Though the above-referenced embodiments refer to animal patients, embodiments of the above-disclosed intranasal administration devices can also be used to nasally administer medicament to human patients. In such embodiments, the spray head, the spray nozzle, and/or the spray apparatus can be made from a substantially rigid material based on the relatively short and uncomplicated intranasal passages to traverse in order to deliver the dose to the target or dose-location coordinate.

In view of the many possible embodiments to which the principles of the disclosure may be applied, it should be recognized that the illustrated embodiments are only preferred examples and should not be taken as limiting the scope of the disclosure. Rather the scope of the disclosure is defined by the following claims.

We claim:

1. An intranasal administration device, comprising:
   a hand-held unit comprising a gripping portion and a spray head, the spray head comprising a spray apparatus and a nozzle configured to administer a discrete dose of medicament in aerosolized form, the nozzle comprising a soft cone configured to fit within a nostril of a non-human patient to prevent dispersion of a spray outside the nostril and to direct spray through the nostril toward an inner tissue, the spray head being removably coupled to the gripping portion;
   a control unit, fluidly coupled to the hand-held unit via one or more flexible connecting tubes configured to resist widening upon a passage of medicament therethrough;
   one or more containers for holding at least one medicament, the one or more containers being removably coupled to the control unit;
   at least one pump located within the control unit, the pump configured to pump medicament from the control unit to the spray apparatus, the pump comprising (i) a first non-return valve, which allows the discrete dose of medicament to pass from the one or more containers to the pump but prevents backflow from the pump to the one or more containers, and (ii) a second non-return valve, which allows the discrete dose of medicament to pass from the pump to the hand-held unit but prevents backflow from the hand-held unit to the pump, wherein the pump comprises a piston, the piston being coupled to an encoder for positioning the piston head to determine a medicament dosage; and
   a mechanism for adjusting spray droplet size of the medicament in aerosolized form.

2. The device of claim 1, wherein the medicament is released automatically when the soft cone has reached a predetermined depth inside the nostril of the non-human patient.

3. The device of claim 1, wherein the spray head comprises a first spray apparatus coupled to a first nozzle and a second spray apparatus coupled to a second nozzle, wherein the first spray apparatus and the first nozzle are configured to move relative to the second spray apparatus and the second nozzle to adjust a distance between them according to a distance between two nostrils of the non-human patient.

4. The device of claim 3, wherein the first spray apparatus and the first nozzle are configured to deliver a first medicament, and the second spray apparatus and the second nozzle are configured to deliver a second medicament.

5. The device of claim 3, wherein the first nozzle and the second nozzle comprise a first soft cone and a second soft cone respectively, and wherein each of the first and second soft cones is configured to: (i) fit the nostril of the non-human patient; (ii) prevent dispersion of the spray outside the nostril; and (iii) direct the spray through the nostril towards an inner mucosal tissue.

6. The device of claim 1, wherein the hand-held unit further comprises a trigger configured to release the discrete dose of medicament in aerosolized form into the nostril of the non-human patient and thereby onto its mucosal tissue.

7. The device of claim 1, wherein urging the spray head rearwardly triggers the release of a predetermined amount of the discrete dose of medicament into the nostril of the non-human patient and thereby onto its mucosal tissue.

8. The device of claim 1, wherein the device is configured to adjust at least one of a distance and a diameter of the discrete dose of medicament in aerosolized form according to an anatomy of the non-human patient.

9. The device of claim 1, further comprising a RFID system configured to record each administration of the discrete dose of medicament.

10. The device of claim 1, further comprising a control panel configured to determine and display information relating to an intranasal administration process.

11. The device of claim 10, wherein the control panel displays a number of non-human patients that have received medicament.

12. The device of claim 1, further comprising an administration indicator for identifying whether a full amount of the discrete dosage of medicament has been delivered.

13. The device of claim 1, further comprising one or more valves, each valve being coupled to a container.

14. The device of claim 1, further comprising a malfunction-identification system.

15. The device of claim 1, wherein the spray head is removably coupled to the gripping portion via a threaded portion on the spray head that engages a correspondingly threaded portion on the gripping portion.

16. The device of claim 1, wherein each of the first and second non-return valves comprises a spring and a stopper and the spring is configured to exert a biasing force against the stopper.

17. The device of claim 1, wherein the mechanism for adjusting spray droplet size of the medicament in aerosolized form comprises a pulse-width modulation controller.

18. The device of claim 1, wherein the mechanism for adjusting spray droplet size of the medicament in aerosolized form is configured to generate droplet sizes ranging from a size greater than 0 μm to a size of 250 μm.

19. The device of claim 1, wherein the mechanism for adjusting spray droplet size of the medicament in aerosolized form is configured to generate droplet sizes ranging from a size greater than 0 μm to a size of 5 μm.

20. The device of claim 1, wherein the discrete dose of medicament comprises between 0.25 ml and 2 ml of the medicament.

21. An intranasal administration device, comprising:
a hand-held unit having a gripping portion and a spray head comprising a spray apparatus and a nozzle, the spray head comprising a spray apparatus and a nozzle configured to administer a discrete dose of medicament in aerosolized form, the nozzle comprising a soft cone configured to fit within a nostril of a non-human patient to prevent dispersion of spray outside the nostril and to direct spray through the nostril toward an inner tissue, the spray head being removably coupled to the gripping portion via a threaded portion on the spray head configured to engage a correspondingly threaded portion on the gripping portion;
one or more dosing chambers fluidly coupled to the spray apparatus;
a control unit fluidly coupled to one or more medicament containers;
at least one flexible connecting tube fluidly coupling the hand-held unit and the control unit, the flexible connecting tube configured to resist widening upon a passage of medicament therethrough;
at least one pump configured to pump medicament from the control unit to the hand-held unit, the pump comprising a first non-return valve configured to allow the dose of medicament to pass from the one or more medicament containers to the control unit and prevent backflow from the control unit to the one or more medicament containers, and a second non-return valve configured to allow the dose of medicament to pass from the control unit to the hand-held unit and prevent backflow from the hand-held unit to the control unit, wherein the pump comprises a piston, the piston being coupled to an encoder for positioning the piston head to determine a medicament dosage;
one or more temperature control units operatively coupled to the one or more medicament containers;
one or more control panels configured to determine and display information relating to an administration process and to transmit real-time data to a remote device;
a malfunction-identification system configured to identify whether a full discrete dose of medicament has been delivered; and
a mechanism for adjusting spray droplet size of the medicament in aerosolized form.

22. A method, comprising:
providing the device according to claim 1; and
using the device to administer a vaccine to a non-human patient.

23. The method according to claim 22 wherein the non-human patient is a livestock animal.

24. The method according to claim 22, wherein the device is an intranasal vaccination device for vaccinating a large number of feed and companion animals selected from swine, cattle, sheep, goats, equids, poultry, cats, dogs, or aquatic species.

* * * * *